(12) United States Patent
Horn et al.

(10) Patent No.: US 6,998,598 B2
(45) Date of Patent: Feb. 14, 2006

(54) MODULAR OPTICAL DETECTOR SYSTEM

(75) Inventors: Brent A. Horn, Livermore, CA (US); Ronald F. Renzi, Tracy, CA (US)

(73) Assignee: Sandia National Labroatories, Livermore, CA (US)

(*) Notice: Subject to any disclaimer, the term of this patent is extended or adjusted under 35 U.S.C. 154(b) by 223 days.

(21) Appl. No.: 10/633,794

(22) Filed: Aug. 4, 2003

(65) Prior Publication Data

US 2005/0023445 A1    Feb. 3, 2005

Related U.S. Application Data

(60) Provisional application No. 60/400,884, filed on Aug. 2, 2002.

(51) Int. Cl.
  *H01J 3/14* (2006.01)
  *H01J 40/14* (2006.01)
  *H01J 5/16* (2006.01)
(52) U.S. Cl. ............... 250/216; 250/239; 250/353
(58) Field of Classification Search ........... 250/216, 250/341.8, 353, 458.1–461.2, 239; 356/4.02, 356/138, 141.3, 150
See application file for complete search history.

(56) References Cited

U.S. PATENT DOCUMENTS 4,432,640 A * 2/1984 Grage et al. ............... 356/4.02
6,838,680 B1 * 1/2005 Maher et al. ............. 250/458.1

* cited by examiner

*Primary Examiner*—David Porta
*Assistant Examiner*—Patrick J. Lee
(74) *Attorney, Agent, or Firm*—Donald A. Nissen

(57) ABSTRACT

A modular optical detector system. The detector system is designed to detect the presence of molecules or molecular species by inducing fluorescence with exciting radiation and detecting the emitted fluorescence. Because the system is capable of accurately detecting and measuring picomolar concentrations it is ideally suited for use with microchemical analysis systems generally and capillary chromatographic systems in particular. By employing a modular design, the detector system provides both the ability to replace various elements of the detector system without requiring extensive realignment or recalibration of the components as well as minimal user interaction with the system. In addition, the modular concept provides for the use and addition of a wide variety of components, including optical elements (lenses and filters), light sources, and detection means, to fit particular needs.

9 Claims, 3 Drawing Sheets

MODULAR OPTICAL DETECTOR SYSTEM

CROSS-REFERENCE TO RELATED APPLICATIONS

This application claims benefit of prior co-pending Provisional Application 60/400,884, filed, Aug. 2, 2002, and entitled A Modular Device for Microscale Biotoxin Detection.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The invention is directed to a modular optical detector system that can be used in combination with capillary chromatographic and microchip-based chemical analysis systems. The presence of molecules or molecular species in liquid mixtures in sub-nanomolar concentrations is determined by inducing fluorescence with exciting radiation and detecting the emitted fluorescence.

BACKGROUND OF THE INVENTION

Recent advances in miniaturization, and particularly in the field of microelectro-mechanical structures (MEMS), have led to the development of microfluidic devices that are designed, in part, to perform a multitude of chemical and physical processes on a micro-scale. The attraction of these microsystems lies in the fact that miniaturization provides for substantial advantages in terms of cost, speed, the capability for easy automation, reproducibility, rapidity of analysis, and the need for only very small ($\mu$L) samples. As a consequence, microsystems in the form of microfluidic devices are becoming increasingly important in such diverse fields as DNA sequencing, immunochromatography, analysis and identification of explosives, chemical and biological warfare agents, and synthesis of chemicals and drugs.

Because only minute amounts of sample are required these microchemical analysis systems are particularly attractive for not only for rapid chemical analysis but also for the ability to analyze accurately a large number of samples in a short period of time. However, there remain problems in reproducibly detecting and measuring low concentrations of chemicals conveniently, safely and quickly.

Laser-induced fluorescence is one of the more sensitive detection methods available, being responsive to picomolar concentrations of analytes and thus, is ideally suited to the small volumes employed in capillary or microchip-based chemical analysis systems.

SUMMARY OF THE INVENTION

Accordingly, an object of this invention is to provide a modular optical detector system for detecting the presence of molecules or molecular species by inducing fluorescence with exciting radiation and detecting the emitted fluorescence. Because the invention is capable of accurately detecting and measuring picomolar concentrations it is designed for use with microchemical analysis systems generally and capillary chromatographic systems in particular.

A further object of the invention is to provide a modular system, wherein modularity is the ability to replace various elements, including optical elements, of the detector system without requiring extensive realignment or recalibration of the components. The modular concept provides for the use of a wide variety of components to fit particular needs. For example, almost any light source that can cause molecules to fluoresce, either naturally or tagged with a fluorophore, can be used in this system. Potential light sources that can be used in the optical detector system can include those that emit light from the infrared to the ultraviolet. These include, but are not limited to light-emitting diodes, laser diodes, vertical cavity surface emitting lasers (VCSELs), vertical external cavity surface emitting lasers (VECSELs), dipole pumped solid state (DPSS) lasers or fiber optic connections that are subsequently coupled to light sources such as large laser systems, laser diodes or lamps. Optical elements can include lenses and filters either singly or in combination, that are totally interchangeable to accommodate the light source. Filters can be put in place to filter out background radiation. More complex optical elements such as blazed or holographic gratings can be included to condition the excitation and emission radiation in ways that cannot be accomplished by filters alone.

Potential detection means for this optical system can include photomultiplier tubes, photodiodes, avalanche photodiodes or array detectors such as photodiode arrays and charge-coupled devices, or photosensitive detectors. These detection means can be run in analog signal collection mode, phase locked, or photon counting mode.

A design feature of the optical detector system is reduced user interaction with the system. By limiting the user interaction to a single mechanical optical adjustment, the time required for aligning the system to a detection region, w herein the detection region can be a portion of a separation channel, is reduced and the potential for user-caused system misalignment is minimized. Once the entire system is initially aligned during assembly, the user need only adjust the lateral position of a beam positioning block using a translation screw for subsequent alignments to the separation channel.

In one embodiment, the invention is directed to an optical detector system that includes:

A light source for generating an exciting light beam;
optical elements for collimating and directing the exciting light beam onto a sample in a detection region and collecting radiation emitted from the detection region; and
detection means for receiving the emitted radiation.

In another embodiment, the light source is a laser, the detection means is a photomultiplier tube and said optical elements, further including a beam steering mirror configuration, are used in conjunction with the laser light source.

DETAILED DESCRIPTION OF THE INVENTION

Figure 1A:
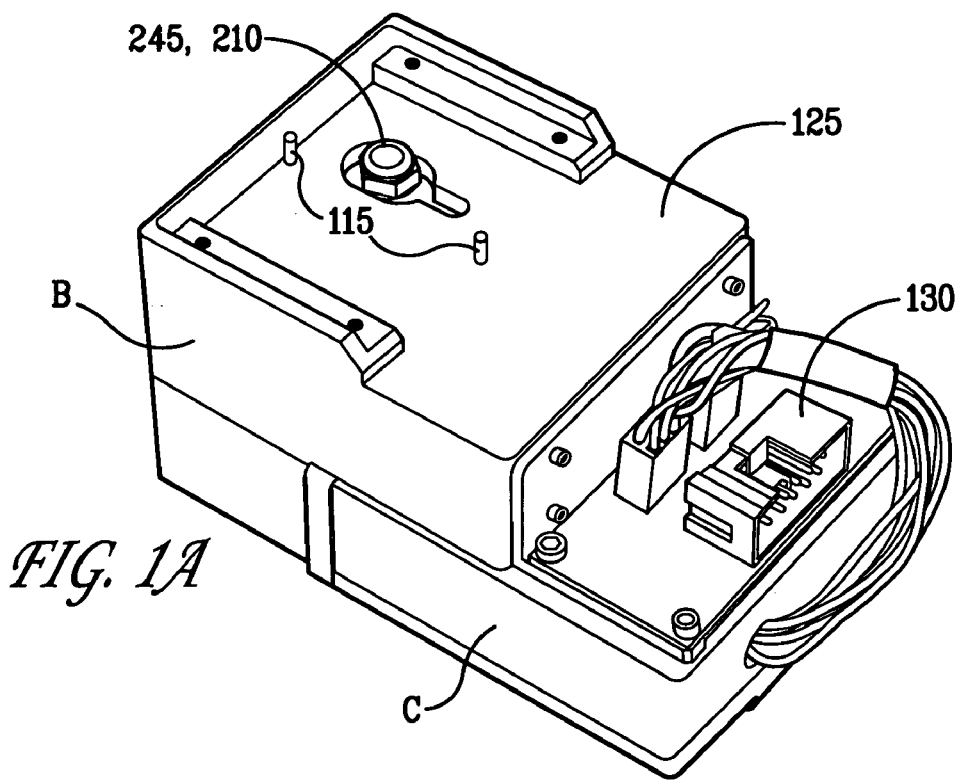
FIG. 1 is a view of an embodiment of the invention showing an exterior view (FIG. 1a) and with the cover removed (FIG. 1b).

Referring now to the drawings, FIG. 1a shows an exterior view of the optical detector system, indicated generally at 100. The optical detector system is comprised generally of two modules, optics module (B) that contains the light source and associated optical elements for generating, collimating, shaping the light beam, directing the resulting light beam onto a detection region, and collecting the resulting fluorescent radiation. Detector module (C) contains detection means for receiving and analyzing the emitted radiation. Module B is in optical communication with module C and, as illustrated in FIG. 1a can be superposed onto module C. The two-tier modular design illustrated in FIG. 1a, wherein the light source and associated optical means are combined with detection means in a unitary structure provides for isolating stray light arising from the excitation source from the detector. Moreover, the totally enclosed package excludes room light. The terms "light" and "radiation" will be used herein interchangeably and synonymously.

Figure 1B:
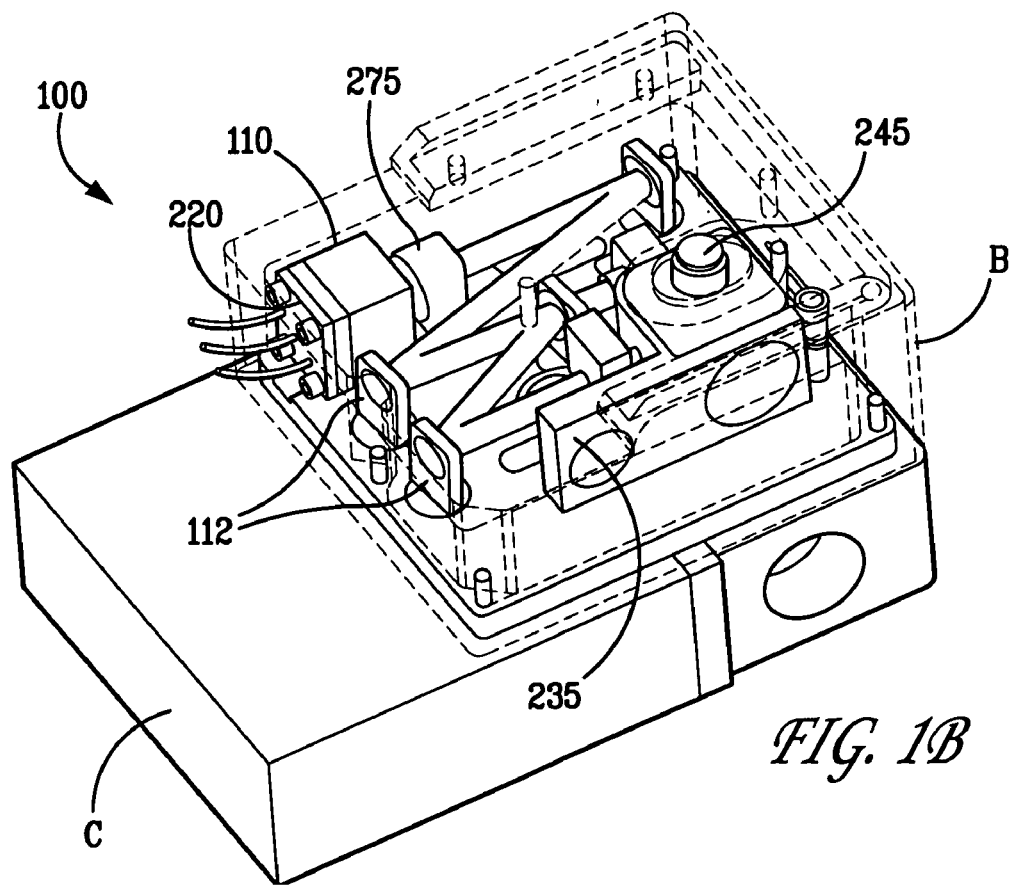

FIG. 1b is a view of the detector system with detector cover 125 removed showing the general arrangement and features of the optics system including excitation source 110, a beam steering mirror system 112, and optical means 245 for focusing exciting radiation onto a sample and for collecting the emitted radiation.

It will be appreciated by those of skill in the optics art, that for analysis purposes is advantageous to employ light that is of the highest quality. Therefore, it is desirable to provide means for proper conditioning of the light beam. FIG. 1b also shows one aspect of the detector system in which beam steering mirror system 112, here comprising four beam steering mirrors, is part of an optical train used, in conjunction with a UV laser light source, to direct light to a detection area, through objective lens 245. The novel folded path provided by this mirror configuration provides an optical path (4.5 to 5 inches) that is long enough so that a light beam can be conditioned properly, both spatially and spectrally within a confined space. For higher quality light sources the beam path can be shortened correspondingly. This steering mirror configuration can provide other advantages such as simplifying alignment of the light beam.

Figure 2:
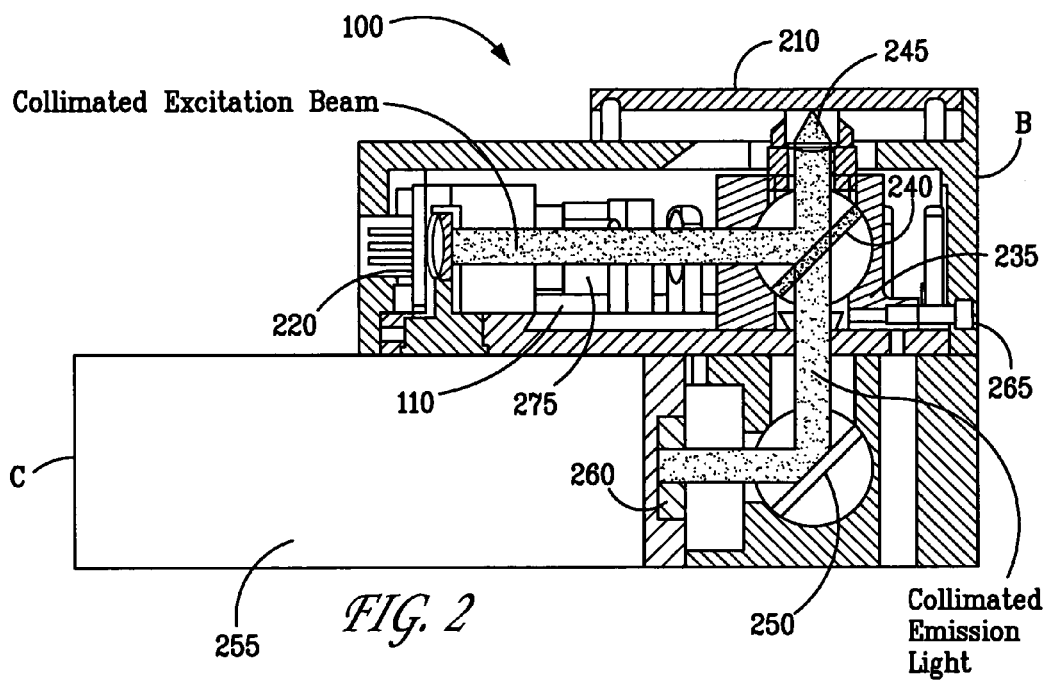
FIG. 2 is an epi-fluorescence configuration of the invention.
Figure 3:
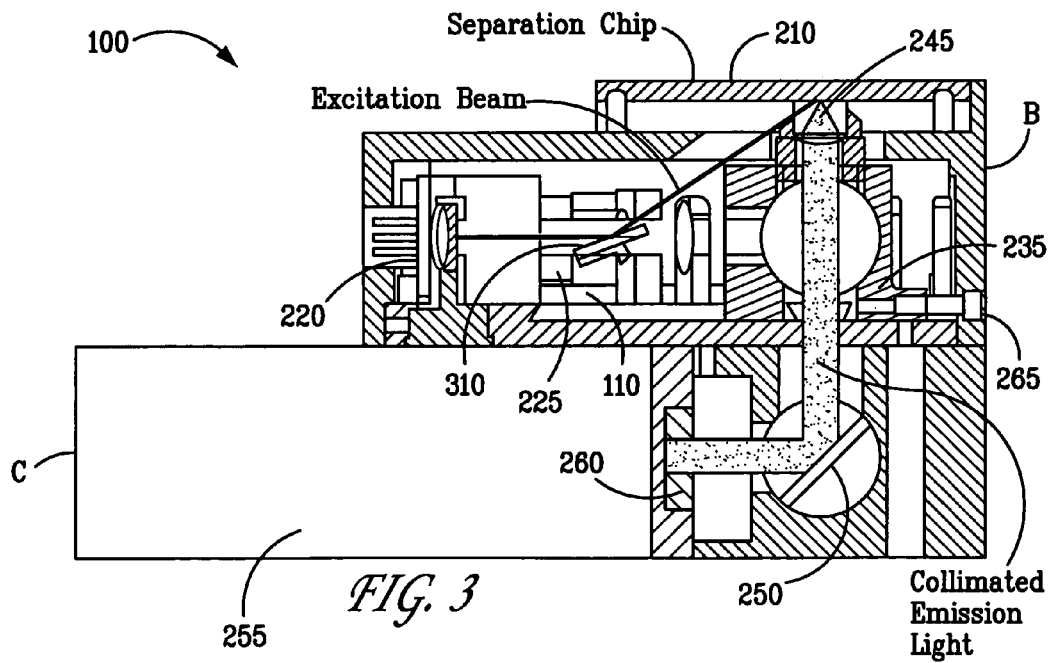
FIG. 3 shows a second configuration for delivering a focused beam of radiation.

FIGS. 2 and 3 are cross-sectional views that illustrate the basic layout of the optical platform for two separate embodiments of the optical detector system. FIG. 2 shows a detector system, in an epi-fluorescence configuration and FIG. 3 shows an off-axis excitation configuration. Both configurations are arranged on a platform that is approximately 3.25 inches long, 2.25 inches wide and 1.3 inches tall.

Referring now to FIG. 2. In this configuration, the detector uses an epi-fluorescence optical configuration to deliver a focused beam of laser light to detection region 210 to excite sample molecules, thereby generating fluorescent radiation. The optics module B of optical detector system 100 contains a light source 220 that can be a generic light source. Potential light sources that could be coupled into this optical detector system are light-emitting diodes, laser diodes, VCSELs, VECSELs, DPSS lasers or fiber optic connections that can be subsequently coupled to light sources such as large laser systems, laser diodes or lamps. In the embodiment shown in FIG. 2 the light source is a laser and preferably a laser capable of generating light having a wavelength of about 405 nm. As discussed above, the collimated beam can be reflected off dichroic reflectors or mirrors 112, to reject some broadband emissions, before being steered onto optical means 240 and 245 contained in beam positioning block 235. Additional excitation filters 275 can be positioned before beam positioning block 235 for increased spectral conditioning. The collimated beam is reflected off a dichroic filter 240 and finally focused onto the detection region 210 that can be the detection region of an associated microfluidic chip or chromatographic column with aspherical lens 245. This same lens is used to collect fluorescence generated by the constituents of the sample in detection region 210. The collimated radiation emitted by the sample is passed through dichroic filter 240 and into detector module C of optical detector system 100 where it can be directed onto radiation detection means, such as a photodetector. In the embodiment illustrated in FIG. 2, the emitted radiation is turned 90 degrees by reflection element 250 into a photodetector 255 that can be a photomultiplier tube. Before passing into the photodetector the collimated beam can be shaped and modified by being passed through filters and optical elements 260. Light from light source 220 can be aligned to the detection area of a microchip or chromatographic column by translating beam steering block 235, and optical means contained therein, back and forth across detection area 210 using translation screw 265. The use of epi-fluorescence provides an additional advantage in that there are no size constraints and thus high numeric aperture (NA) aspheric or ball-type lenses can be used as a collection optic. In one aspect of the invention, a 0.60 NA aspheric lens was used as the collection optic.

In a second embodiment (FIG. 3), a focused beam of light is delivered onto the detection region 210 at Brewster's angle for fused silica and the radiation emitted therefrom is collected and analyzed. Excitation light from light source 220, is collimated by aspherical lens 225. As in the embodiment above, the light source can be a generic light source. As before, light sources that could be coupled into this optical detector system are light-emitting diodes, laser diodes, VCSELs, VECSELs, DPSS lasers or fiber optic connections that can be subsequently coupled to light sources such as large laser systems, laser diodes or lamps. Here, as above, a laser having a wavelength of about 405 nm is used as a source of exciting radiation. To reject broadband emissions from light source 220, excitation filters 275 can be positioned between the light source and beam steering mirror 310 to spectrally modify the collimated light beam. Turning mirror 310, attached to an arm or beam positioning block 235, is used to direct the beam upward to intersect detection region 210 directly above and centered on objective lens 245. Transition screw 265 is used to translate beam steering block 235, containing lens 245 and mirror 310, laterally so the focused light beam and lens are positioned properly with respect to detection region 210. In order to ensure that the light beam is intersecting the detection region, a fluorescent dye can be injected into the detection region to visualize the location of the beam. Lens 245 is used to collect the fluorescent radiation emitted from the detection region. As in the embodiment above, the collected fluorescent radiation is directed to the detector module (module C) of the optical detector system where the collected light passes through filters and lenses 260 to remove scattered and off-wavelength radiation and into a radiation detection means such as photomultiplier tube 255.

Figure 4:
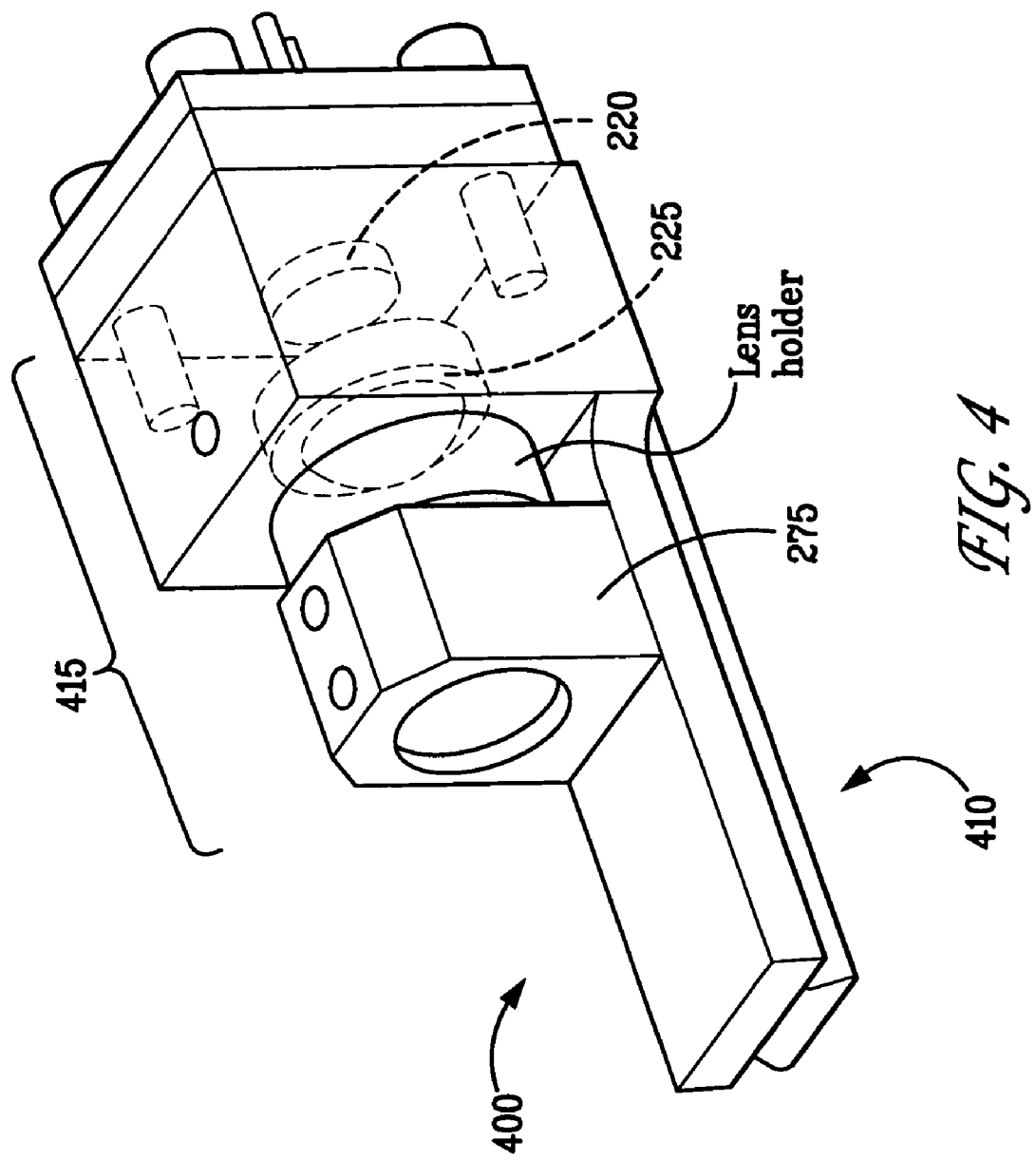
FIG. 4 shows a dovetail rail assembly for holding the excitation source.

In keeping with an object of the invention, the ability to replace components without the necessity of realignment or recalibration, FIG. 4, shows a dovetail-aligned rail assembly, indicated generally at 400. This assembly is a unitary structure that holds an excitation source 415, wherein said excitation source comprises light source 220 and associated collimating optics 225 and filters 275 in a stable, fixed relationship with one another and wherein the excitation source is demountably engaged on dovetail rail 410. Not only does this unique feature provide for easy replacement of the light source and/or optics but also ensures that established alignment will be maintained if the rail assembly or any of its components are replaced.

A design feature of the optical detector system is reduced user interaction with the system. In this regard, optics module B incorporates a beam positioning block 235, wherein said beam positioning block includes, at least, dichroic filter 240 and focusing/collection optic 245. By limiting the user interaction to a single mechanical adjustment, the time required for aligning the system to a detection area is reduced and the potential for user-caused system failure is eliminated. Once the entire system is initially aligned, the user need only adjust the lateral position of beam positioning block 235 using translation screw 265 for subsequent alignments to a detection area. Alignment pins 115 are incorporated into the detector lid to reduce the magnitude of the adjustment made to translation screw 265 to achieve proper alignment.

It is contemplated that the novel modular optical detector system disclosed herein could be used in conjunction with a microfluidic chemical analysis system and in particular with capillary chromatography systems.

We claim:

1. A modular optical detector system, comprising:
   a first module, wherein said first module comprises;
     an excitation source including a light source, collimating optics and filters, and
     optical elements for modifying light from said light source and directing the modified light onto a detection region and collecting radiation emitted therefrom, wherein the components of the excitation source are demountably engaged on a dovetail rail, such that the components of the excitation source are maintained in a fixed and stable orientation; and
   a second module, wherein said second module comprises detection means for receiving and analyzing the emitted radiation, and wherein the first module is superposed on said second module.

2. The modular optical detector system of claim 1, wherein the light source provides light having a wavelength ranging from the infrared to the ultraviolet.

3. The modular detector system of claim 2, wherein said light source includes lasers, light-emitting diodes, laser diodes, vertical cavity surface emitting lasers, vertical external cavity surface emitting lasers, or dipole pumped solid state lasers.

4. The modular detector system of claim 3 wherein the laser produces light having a wavelength of about 405 nm.

5. The modular optical detector system of claim 1, further including a beam positioning block and alignment pins that provide for proper positioning of said optical elements with respect to a detector area.

6. The modular optical detector system of claim 1, wherein the optical elements include means for conditioning of the light.

7. The modular detector system of claim 6, wherein means for conditioning of the light comprises a beam steering mirror system.

8. The modular detector system of claim 1, wherein the detection means comprises photomultiplier tubes, photodiodes, avalanche photodiodes, array detectors, charge-coupled devices, or photosensitive detectors.

9. The modular detector system of claim 7, wherein the beam steering mirror system comprises a 4 mirror system.

* * * * *